(12) United States Patent
Schipper et al.

(10) Patent No.: US 10,517,517 B2
(45) Date of Patent: Dec. 31, 2019

(54) OPTICAL ANALYSIS SYSTEM AND METHOD

(71) Applicant: KONINKLIJKE PHILIPS N.V., Eindhoven (NL)

(72) Inventors: Alphonsus Tarcisius Jozef Maria Schipper, Stramproy (NL); Koen Geenen, Gilze (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 262 days.

(21) Appl. No.: 15/563,726

(22) PCT Filed: Mar. 30, 2016

(86) PCT No.: PCT/EP2016/056835
§ 371 (c)(1),
(2) Date: Oct. 2, 2017

(87) PCT Pub. No.: WO2016/156341
PCT Pub. Date: Oct. 6, 2016

(65) Prior Publication Data
US 2018/0085039 A1    Mar. 29, 2018

(30) Foreign Application Priority Data
Apr. 2, 2015    (EP) ..................................... 15162451

(51) Int. Cl.
*A61B 5/1455* (2006.01)
*A61B 5/00* (2006.01)
*A61B 5/024* (2006.01)
*A61B 5/026* (2006.01)
*A61B 5/0205* (2006.01)

(52) U.S. Cl.
CPC ........ *A61B 5/14551* (2013.01); *A61B 5/0205* (2013.01); *A61B 5/0261* (2013.01); *A61B 5/02416* (2013.01); *A61B 5/7203* (2013.01); *A61B 5/7225* (2013.01); *A61B 5/7242* (2013.01)

(58) Field of Classification Search
None
See application file for complete search history.

(56) References Cited

U.S. PATENT DOCUMENTS

| | | |
|---|---|---|
| 2004/0030231 A1 | 2/2004 | Norris |
| 2007/0100218 A1 | 5/2007 | Sweitzer et al. |
| 2009/0299675 A1 | 12/2009 | Isaacson et al. |
| 2014/0275878 A1 | 9/2014 | Lisogurski |
| 2014/0323844 A1 | 10/2014 | Deliwala et al. |

FOREIGN PATENT DOCUMENTS

| | | |
|---|---|---|
| JP | H0242338 A | 2/1990 |
| JP | H09288785 A | 11/1997 |

Primary Examiner — Eric F Winakur
Assistant Examiner — Marjan Fardanesh

(57) ABSTRACT

An optical analysis system and method is provided in which a sample is analyzed using a light source. An optical sensor signal is processed using a first signal processing circuit and an electrical signal, which is representative of a drive signal applied to the light source, is processed using a second signal processing circuit. The sensor signal is further processed to improve the signal to noise ratio using the processed electrical signal as a reference.

12 Claims, 3 Drawing Sheets

OPTICAL ANALYSIS SYSTEM AND METHOD

This application is the U.S. National Phase application under 35 U.S.C. § 371 of International Application No. PCT/EP2016/056835, filed on Mar. 30, 2016, which claims the benefit of European Application No. 15162451.7, filed Apr. 2, 2015. These applications are hereby incorporated by reference herein.

FIELD OF THE INVENTION

The invention relates to the optical analysis of samples, for example a body part. Examples of optical analysis include photoplethysmogram-based heart rate derivation or determination of oxygenation of arterial blood by pulse oximetry (SpO2).

BACKGROUND OF THE INVENTION

Photoplethysmograph (PPG) sensors such as heart rate monitors or pulse oximeters are widely used in medical, wellness and sports areas. They generally use an artificial light source such as an LED that emits light into the skin of a user. The emitted light is scattered within the skin, where it is absorbed partially by blood. Reflected or transmitted light exits the skin and is captured by a photodetector. As a consequence, the signal of the photo detector is an indication of the blood volume. When the blood stream pulsates, the blood volume in the skin changes. Thus, the signal on the photodetector changes directly in response to the pulsation. Hence, the sensor measures directly a pulse of the user in the skin and can thus determine the actual heart rate of the user at a particular moment.

Blood oximeters, especially pulse oximeters, are widely used for measuring oxygenation of blood of a patient. They provide a simple non-invasive method for monitoring the percentage of hemoglobin which is saturated with oxygen. Continuous monitoring of oxygen saturation via pulse oximetry is a standard care procedure used in operating rooms, post anesthesia care units, critical care units and emergency departments.

A pulse oximeter typically comprises two light-emitting diodes or a set of light emitting diodes that emit light of different wavelengths, typically in the red and the infrared part of the spectrum, respectively. The part of the emitted light transmitted through or reflected by tissue of a part of the patient's body, typically a fingertip or an ear lobe, is collected with a photodetector, usually a photodiode.

Absorption of these different wavelengths differs between oxyhemoglobin and its deoxygenated form, so that from the ratio of the collected red and infrared light, the percentage of hemoglobin which is saturated with oxygen can be determined.

In these current systems for optical heart rate measurement and measurement of oxygen saturation, an LED is typically used as the source of light. The signal-to-noise ratio of the collected light signal (after reflection or transmission by the sample) is limited by the signal to noise ratio of the LED source. For this reason, a relatively high quality LED driver is required. Typically, such LED driver circuits require a signal-to-noise ratio of more than 80 dB.

As systems for optical heart rate and oxygen saturation measurement become more common, cost becomes more important. For example, it is proposed to use pulse monitoring systems in watches. Power consumption therefore becomes more important as well.

Having a lower cost and lower power LED driver becomes therefore more important. There is therefore a need to enable a low cost and low power LED and LED driver combination which enables signals of sufficiently high signal to noise ratio to be obtained. The LED driver is responsible for a significant part of the system cost and system power so that reductions in the complexity of the LED driver are particularly desirable. Similarly, a lower cost driver for a laser diode will produce a more noisy laser diode output, so that same issues arise for other types of light source such as laser diodes.

SUMMARY OF THE INVENTION

The invention is defined by the claims.

According to examples in accordance with an aspect of the invention, there is provided an optical analysis system, comprising:

a light source for illuminating a sample to be analyzed;

a driver for operating the light source;

a photodetector for receiving light reflected by or transmitted through the sample to be analyzed and generating a sensor signal;

a first signal processing circuit for processing the sensor signal and which comprises a transimpedance amplifier;

a second signal processing circuit for processing an electrical signal provided by the driver which is representative of the drive signal applied to the light source, wherein the second signal processing circuit comprises a filter having a filter frequency characteristic which corresponds to the frequency transfer characteristic of the transimpedance amplifier; and a compensation circuit for further processing the sensor signal to improve the signal to noise ratio using the processed electrical signal.

The electrical signal provided by the driver functions as a monitor signal, which is indicative of the quality of the light output, since it is based on the light source driver signal. This monitor signal is processed with a transfer function which as closely as possible corresponds to the transfer function of the processing of the photodetector signal. Thus, there is processing of the light source drive signal purely in the electrical domain as well as processing in a signal path which includes the electro-optic conversion by the light source and the opto-electric conversion by the photodetector. The further processing of the sensor signal implements a cancellation function, which is able to cancel out the noise caused by the light source driver.

The light source may comprise an LED arrangement and the drive signal is a drive current driven through the LED arrangement. The system is therefore able to cancel out LED driver noise, such that a low cost and low-power LED driver is enabled.

The first signal processing circuit comprises a transimpedance amplifier. This performs a current to voltage conversion of the photodetector current.

The second signal processing circuit comprises a filter having a filter frequency characteristic which corresponds to the frequency transfer characteristic of the transimpedance amplifier. For example, the transimpedance amplifier typically has a low pass filter characteristic, and the filter used for processing the electrical signal is selected to provide a corresponding filtering function.

The first signal processing circuit may comprise a first integrator circuit and a first analog to digital converter. The integrator is used to collect a signal over a predetermined time duration. The second signal processing circuit preferably comprises a second integrator circuit which corresponds to the first integrator circuit and a second analog to digital converter. In this way, the processing of the electrical signal and the processing of the photodetector signal are matched as closely as possible, so that any noise frequency spectrum present in the photodetector signal has a counterpart in the processed electrical signal.

The first and second integrator circuits and the first and second analog to digital converters are for example controlled with the same timing signals.

The compensation circuit may comprise:

a normalizing circuit for normalizing the processed electrical signal and providing a multiplier which is the reciprocal of the normalized processed electrical signal; and a scaling element which provides a scaling factor corresponding to the multiplier.

The normalizing circuit extracts the variations in the processed electrical signal. By inverting these to form a gain multiplier, any corresponding variations in the processed photodetector signal are cancelled.

The electrical signal for example comprises a voltage across a current sense resistor through which the current of the light source is passed. For example, it provides a direct representation of an LED current, including any noise caused by the LED driver.

Other electrical signals may be used. For example, a current signal may be generated using a current mirror. The signal processing paths for the photodetector current and the mirrored current may again be matched.

The driver may comprise a drive transistor to which a control voltage (transistor gate or base) is applied to generate a current through the light source. This provides a basic driver architecture. Noise resulting from the basic transistor circuit can be compensated by the circuit design.

The system may be part of an oximeter or an optical heart rate monitor. The oximeter or optical heart rate monitor will of course include other functional units, for example for processing the captured signals.

The invention also provides an optical analysis method, comprising:

illuminating a sample to be analyzed using a light source;

receiving light reflected by or transmitted through the sample to be analyzed and generating a sensor signal in response thereto;

processing the sensor signal using a first signal processing circuit which comprises a transimpedance amplifier;

processing an electrical signal which is representative of a drive signal applied to the light source using a second signal processing circuit wherein the second signal processing circuit comprises a filter having a filter frequency characteristic which corresponds to the frequency transfer characteristic of the transimpedance amplifier; and further processing the sensor signal to improve the signal to noise ratio using the processed electrical signal.

A processed electrical signal from the driver is used to compensate for noise which has been introduced into the optical signal (i.e. the LED output) by the light source driver. The processing of the sensor signal and the processing of the electrical signal may be based on corresponding frequency transfer functions.

The further processing for example comprises normalizing the processed electrical signal, providing a multiplier which is the reciprocal of the normalized processed electrical signal, and providing a gain corresponding to the multiplier.

BRIEF DESCRIPTION OF THE DRAWINGS

Examples of the invention will now be described in detail with reference to the accompanying drawings, in which.

DETAILED DESCRIPTION OF THE EMBODIMENTS

The invention provides an optical analysis system and method in which a sample is analyzed using a light source. An optical sensor signal is processed using a first signal processing circuit and an electrical signal, which is representative of the drive signal (e.g. drive current) applied to the light source, is processed using a second signal processing circuit. The sensor signal is further processed to improve the signal to noise ratio using the processed electrical signal as a reference.

Figure 1:
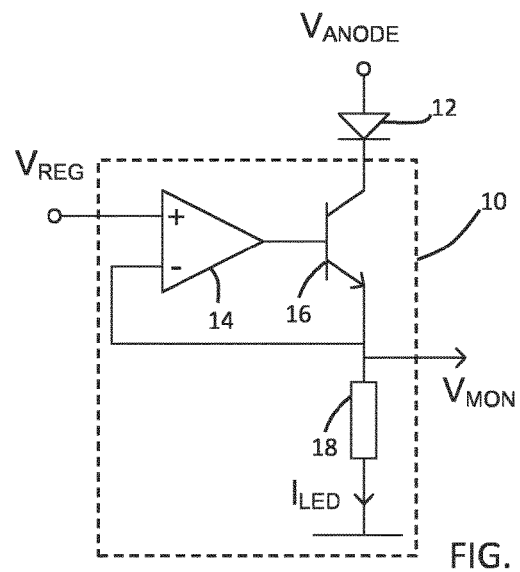
FIG. 1 shows a basic LED driver which may be used as part of the optical analysis system.

FIG. 1 shows an example of a simple implementation of an LED driver 10 for generating a drive current which flows through a light source in the form of an LED arrangement 12. The driver 10 comprises a drive transistor 16 to which a controlled base voltage is applied to generate a current through the LED arrangement. A regulation voltage $V_{REG}$ is applied to the non-inverting input of an operational amplifier 14, and the emitter voltage is fed back to the inverting input of the amplifier 14.

The drive current $I_{LED}$ passes through a sense resistor 18 (of resistance R), and the voltage across the sense resistor 18 functions as a monitor signal $V_{MON}$.

The operational amplifier regulates the voltage across the resistor 18 such that it is equal to the regulation voltage $V_{REG}$.

The signal to noise ratio of the drive current typically is desired to be greater than 80 dB. For this to happen, the signal to noise ratio of $V_{REG}$ must be at least as high. Also, the supply voltage $V_{ANODE}$ must be from a regulated source, such that it does not drop too low, that is: $V_{ANODE} > I_{LED} * R + V_{CE} + V_{LED}$.

$V_{LED}$ is the voltage drop over the LED and $V_{CE}$ is the collector-emitter voltage of the transistor.

Generally, a boost converter is required to generate $V_{ANODE}$. The boost converter must be designed such that sufficient voltage is generated under all circumstances, including peak currents.

The monitor signal $V_{MON}$ is proportional to the LED current $I_{LED}$. Any decrease in signal to noise ratio of the LED current is represented in this monitor signal. If there is noise in $V_{REG}$, then the noise will be in the LED current and therefore also in the monitor signal. If $V_{ANODE}$ temporarily drops too low then it will cause noise in the LED current and therefore also in the monitor signal.

If a small current sense resistor 18 is desired, an amplifier may be used increase the amplitude of $V_{MON}$.

The invention provides a system which relaxes the requirements on the supply and control voltages used in the driver circuit of FIG. 1 by providing active cancellation of signal noise.

Figure 2:
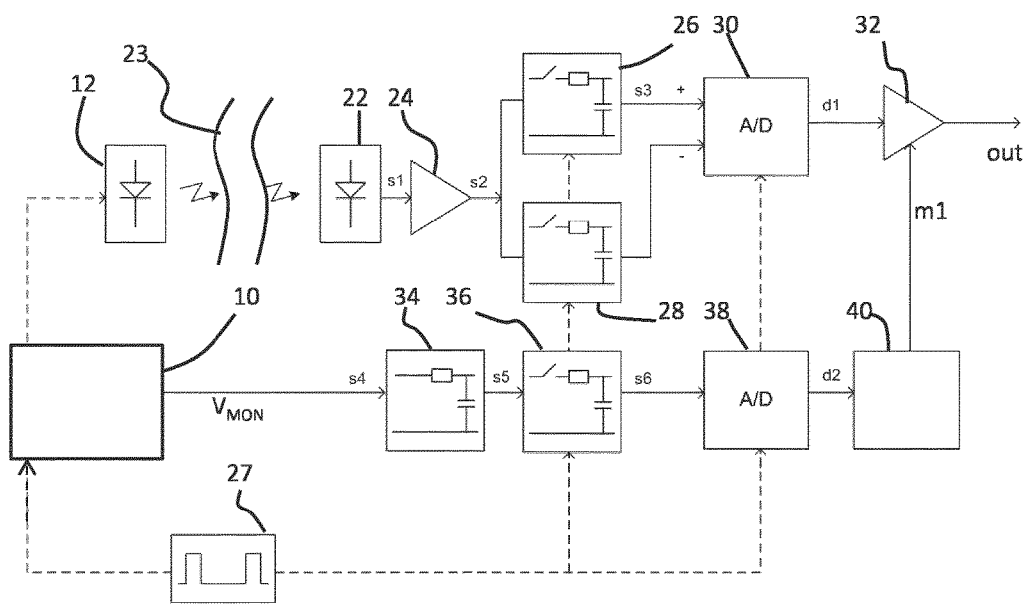
FIG. 2 shows an optical analysis system.

FIG. 2 shows a diagram of the system.

The LED arrangement 12 emits pulsed light and a photodetector (e.g. a photodiode) 22 collects the light after reflection or transmission through a sample 23 to be analyzed, which is typically a finger, ear lobe, wrist or other body part.

The photodetector 22 generates a first electrical current signal s1 which is amplified by a transimpedance amplifier (TIA) 24. This performs a current to voltage conversion and amplification to generate voltage signal s2.

The amplifier 24 has a low-pass behavior.

The signal pulse s2 is integrated using a main integrator 26 to generate signal s3. The integration is timed synchronously with the generation of the light pulse. This timing is shown as 27.

After integration, the main signal s3 is converted to digital form by an A/D converter 30, resulting in digital signal d1.

In addition to the main integrator 26, an ambient signal integrator 28 is used to integrate the signal detected by the photodetector at times when the LED pulse is off. This ambient light signal is subtracted from the main signal in the A/D converter block 30 prior to A/D conversion. This aspect is not relevant for the noise cancellation method described below, which concerns only the time periods of operation of the LED driver.

The amplifier 24, integrators 26,28 and analog to digital converter 30 may together be considered to define a first signal processing circuit for processing the sensor (i.e. photodetector) signal.

Noise from the LED driver will be present in signal d1. The sampling rate of signal d1 is equal to the sampling rate of the timing generator, which may for example be 128 Hz. The noise in the LED driver may typically have higher frequencies than the sampling rate. However, this noise folds back into signal d1 due to aliasing. This means that wideband noise in the LED driver may cause the signal d1 to be noisy.

The monitor signal $V_{MON}$ from the LED driver 10 is fed into a separate monitor channel. This signal is shown as s4.

The monitor channel comprises a low pass filter 34, a monitor signal integrator 36 and an A/D converter 38.

The low pass filter 34 has the same low pass characteristic as the transconductance amplifier 24. More generally, the filter 34 has a filter frequency characteristic which corresponds to the frequency transfer characteristic of the transimpedance amplifier.

The signals s1 and s4 will of course be different. Signal s1 will contain additional noise resulting from the electrical to optical conversion, from the optical to electrical conversion and from the optical signal path. These additional noise sources will not be cancelled out. Examples of sources of such noise include ambient light, variations in optical contact, motion artifacts, etc. However, the tissue being analyzed remains a linear medium and as such the LED current variations directly translate into variations of s1. There is thus not a significant frequency transfer function resulting from the light interaction with the sample.

The monitor integrator 36 has the same characteristic as the main integrator 26 and runs synchronously with it, using the same timing signal 27. As a result, the noise in the processed and digitized monitor signal d2 is proportional to the noise in the processed and digitized sensor signal d1, including any noise due to aliasing. This is the case because the noise in the monitor signal s4 is proportional to the noise in the light signal s1, and the frequency transfer function characteristics of the monitor channel and main sensor channel are designed to be the same. The monitor channel and main sensor channel are operated synchronously.

The signal d2 is normalized so that it has a unity DC level with a noise signal superposed over the top. A reciprocal is then taken. These steps are carried out in the processing block 40. The signal is normalized by low pass filtering to extract the DC content, and scaling is carried out as a function of the DC level. The reciprocal value is then taken. The processing block 40 may thus be considered to be a normalizing circuit. In practice, this normalizing comprises digital signal processing and the processing block is for example a digital signal processor.

The output of the processing block 40 is a multiplier m1, and it is used to control a variable gain amplifier 32, which multiplies the signal d1 with the multiplier m1 to yield the output "out". This variable gain amplifier 32 may be considered to be scaling element, in that it may apply a gain of less than unity or greater than unity. The multiplier m1 is then a scaling factor.

The processing block 40 and the variable gain element 32 may together be considered to define a compensation circuit which further processes the sensor signal d1 to improve the signal to noise ratio using the processed electrical signal d2.

The LED driver noise is thus cancelled out.

Figure 3:
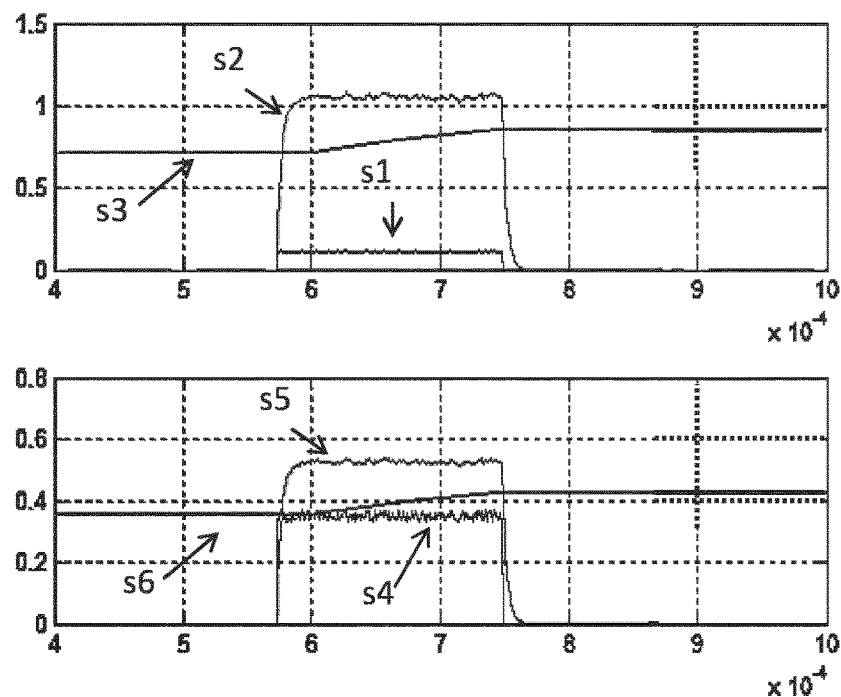
FIG. 3 shows timing diagrams to explain the operation of the circuit of FIG. 3.

FIG. 3 shows waveforms during an LED pulse.

The top graph shows the signals in the main channel, in particular the input s1 to the transimpedance amplifier 24, the output s2 of the transimpedance amplifier, and the output s3 of the main integrator 26.

The gain of the transimpedance amplifier is clearly seen as well as the integration function.

The bottom graph shows the signals in the monitor channel, in particular the monitor signal s4 (i.e. $V_{MON}$ in FIG. 1), the output s5 of the low pass filter 34 and the output s6 of the monitor integrator 36.

The filtering function can be seen, with a reduction in high frequency ripple.

The switches of the main integrator 26 and the monitor integrator 36 are closed from $t \approx 5.8 \times 10^{-4}$ to $7.5 \times 10^{-4}$s. During this interval, both the filtered monitor signal s5 and the transimpedance amplifier output signal s2 are integrated.

Figure 4:
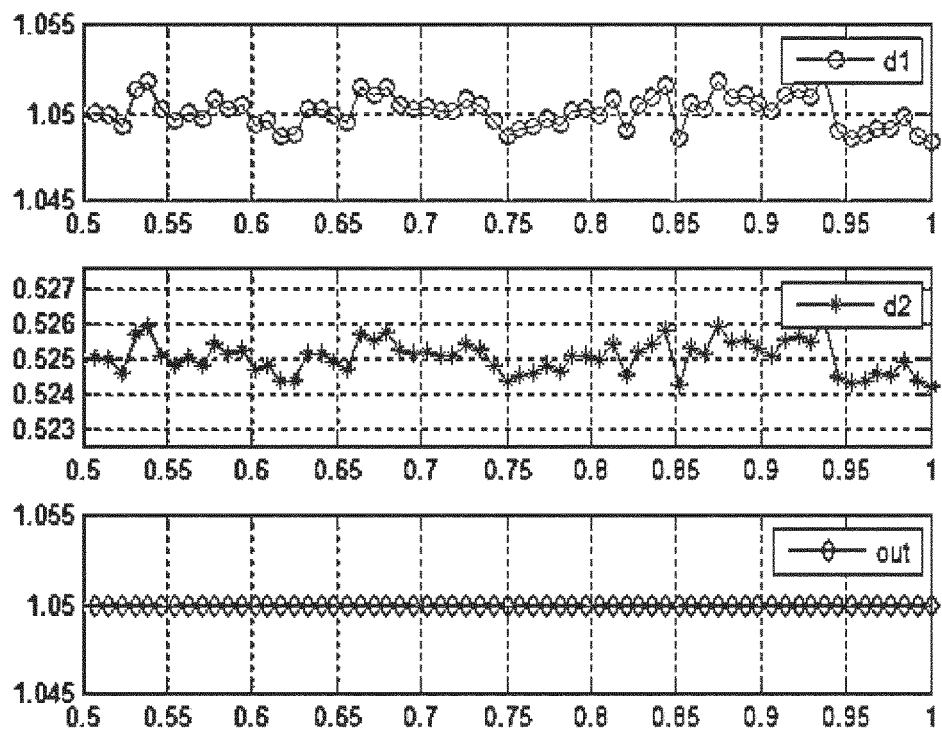
FIG. 4 shows timing diagrams to demonstrate the benefit of the circuit of FIG. 3.

FIG. 4 shows the signals d1, d2 and "out".

The signal d1 is the sensed signal including a noise component resulting from the LED driver noise. Signal d2 is the signal with the corresponding noise as processed in the monitor channel. Signal "out" is the signal in which the noise has been cancelled out.

FIG. 4 shows that the signals d1 and d2 have different magnitudes, as the two channels are not identical. The sensor signal includes amplification in the transimpedance amplifier 24, and it also include the two opto-electrical conversion steps as well as signal attenuation in the sample. However, the frequency transfer characteristics of the two channels to the noise component is designed to be the same.

By normalizing the signal d2, the noise shape is preserved and this noise shape is then used for cancelling the corresponding noise present in the sensor signal d2. As shown, the resulting output signal is substantially noise free.

In this way, an electrical processing channel and an optical processing channel are combined to enable noise cancellation.

The invention can be applied to pulse oximetry systems as explained above, but also to optical analysis systems generally, where LED driver noise is an issue.

Apart from measuring heart rate and oxygen saturation (SpO2), other blood constituents may be measured such as glucose or total hemoglobin, carboxyhemoglobin, methemoglobin, perfusion index or pleth variability index.. It is also known that the respiration rate can be derived from a PPG signal.

The sample being analyzed does not have to be a body part. Systems which optically detect the presence or measure the concentration of other targets within a medium, for example bacteria in a sample such as milk, may also benefit from the improved signal to noise ratio enabled by the invention..

The use of a voltage across a current sense resistor as the electrical signal provided by the driver is one example only. The electrical signal may be any signal which includes the same noise as will be present in the light output. The electrical signal may for example comprise a current from a current mirror.

The single transistor LED driver is only one example of simple current driver circuit which may be used. Other LED drivers may be used. For example, regulation using an operational amplifier is not essential, and other transistor circuits or diode-transistor circuits may be used. The invention can be employed as long as an electrical signal can be extracted from the driver which includes a noise component corresponding to the noise in the optical output.

A heart rate monitor system based on PPG may use only single wavelength of light, such as a green light at 525 nm wavelength. Such a device may function as a reflective PPG sensor designed to be worn on the wrist.

A heart rate monitor may also make use of multiple wavelengths of light and the extra information may for example be used to reduce artifacts for example caused by motion.

In pulse oximetry systems for measuring oxygen saturation, the LED arrangement is typically for generating light in the red and infrared bands. The LED arrangement may have separate LEDs for different frequency bands or it may comprise a broad spectrum LED for providing illumination in both bands. Similarly, the photodetector is responsive to light in both bands, and it may include separate detecting surfaces or a single broadband detecting surface.

In most systems, red and infrared pulses are sent in sequence (usually also with an intervening period with no active illumination in order to measure the influence of ambient light), but the illumination may also be simultaneous. There may then be two photodetectors that have different sensitivity spectra.

When multiple wavelengths are time multiplexed, the circuitry shown in FIG. 2 is basically repeated, apart from the wideband photodetector and transimpedance amplifier which may be shared across the wavelengths.

Figure 5:
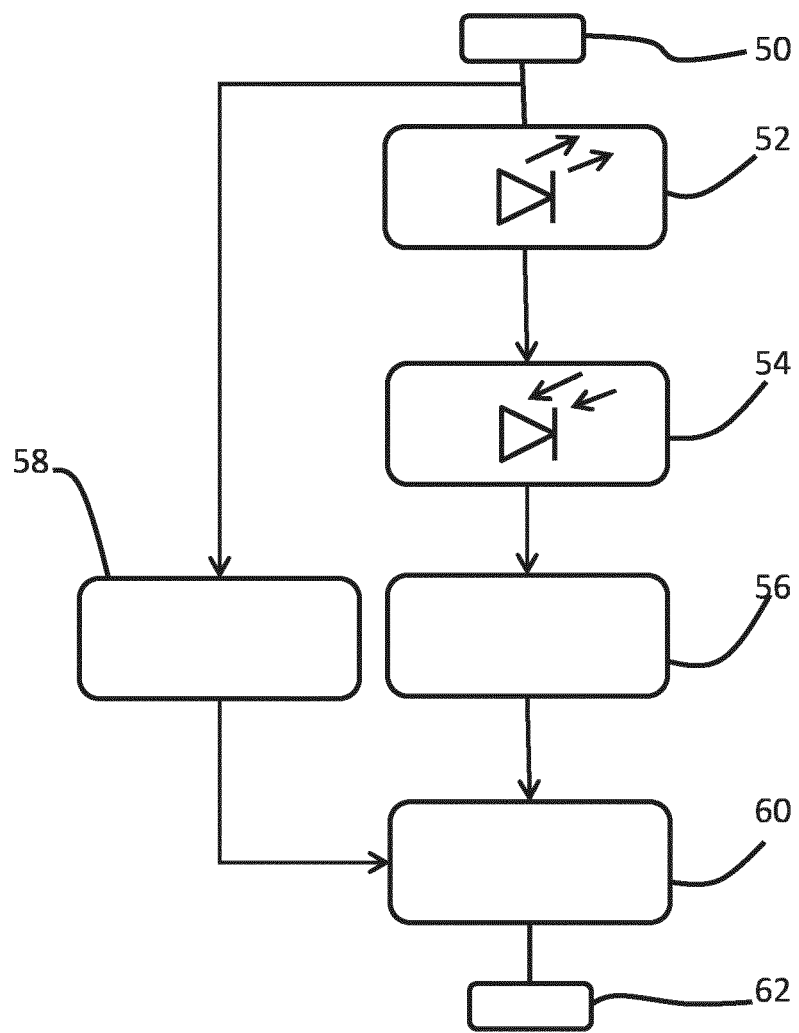
FIG. 5 shows an optical analysis method.

FIG. 5 shows the method of optical analysis. The process starts in step 50.

In step 52, a sample to be analyzed is illuminated using a light source, such as an LED arrangement, by applying a drive signal, for example by driving a current through the LED arrangement.

In step 54, light reflected by or transmitted through the sample to be analyzed is received by a photodetector and a sensor signal is generated in response.

In step 56 the sensor signal is processed using a first signal processing circuit.

In step 58 an electrical signal (provided by the driver 10) which is representative of the drive signal applied to the light source, such as the current driven through the LED arrangement, is processed using a second signal processing circuit.

In step 60 the sensor signal is further processed to improve the signal to noise ratio using the processed electrical signal. The process ends in step 62.

The light source is typically an LED arrangement as described above, but a laser light source may also be used such as a laser diode. This does not change the way the noise cancellation functions. In particular, noise in a drive signal applied to the laser diode (e.g. a regulated current, a regulated voltage or a combination thereof) will cause noise in the optical output. The system of the invention again enables this noise to be largely cancelled. It will be seen that the drive signal may be a current and/or a voltage.

The photodetector may be a single photodiode, or an array of photodiodes, or another light sensing technology such as a charge coupled device.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measured cannot be used to advantage. Any reference signs in the claims should not be construed as limiting the scope.

The invention claimed is:

1. An optical analysis system, comprising:
   a light source for illuminating a sample to be analyzed;
   a driver for operating the light source;
   a photodetector for receiving light reflected by or transmitted through the sample to be analyzed and generating a sensor signal;
   a first signal processing circuit for processing the sensor signal and which comprises a transimpedance amplifier;
   a second signal processing circuit for processing an electrical signal provided by the driver which is representative of the drive signal applied to the light source; and
   a compensation circuit for further processing the sensor signal to improve the signal to noise ratio using the processed electrical signal, characterized in that the second signal processing circuit comprises a filter having a filter frequency characteristic which corresponds to the frequency transfer characteristic of the transimpedance amplifier.

2. A system as claimed in claim 1, wherein the first signal processing circuit comprises a first integrator circuit and a first analog to digital converter.

3. A system as claimed in claim 2, wherein the second signal processing circuit comprises a second integrator circuit which corresponds to the first integrator circuit and a second analog to digital converter.

4. A system as claimed in claim 3, wherein the first and second integrator circuits and the first and second analog to digital converters are controlled with the same timing signals.

5. A system as claimed in any preceding claim, wherein the compensation circuit comprises:
   a normalizing circuit for normalizing the processed electrical signal and providing a multiplier which is the reciprocal of the normalized processed electrical signal; and
   a scaling element which provides a scaling factor corresponding to the multiplier.

6. A system as claimed in claim 1, wherein the electrical signal comprises a voltage across a current sense resistor through which a drive current of the light source is passed.

7. A system as claimed in claim 1, wherein the driver comprises a drive transistor to which a control voltage is applied to generate a current through the light source.

8. A system as claimed in claim 1, comprising:
   an oximeter; or
   an optical heart rate monitor.

9. An optical analysis method, comprising:
illuminating a sample to be analyzed using a light source;
receiving light reflected by or transmitted through the sample to be analyzed and generating a sensor signal in response thereto;
processing the sensor signal using a first signal processing circuit which comprises a transimpedance amplifier;
processing an electrical signal which is representative of a drive signal applied to the light source using a second signal processing circuit wherein the second signal processing circuit comprises a filter having a filter frequency characteristic which corresponds to the frequency transfer characteristic of the transimpedance amplifier; and
further processing the sensor signal to improve the signal to noise ratio using the processed electrical signal.

10. A method as claimed in claim 9, wherein the processing of the sensor signal and the processing of the electrical signal are based on corresponding frequency transfer functions.

11. A method as claimed in claim 9, wherein the processing of the sensor signal and the processing of the electrical signal comprise signal integration and analog to digital conversion, controlled with the same timing signals.

12. A method as claimed in claim 9, wherein the further processing comprises normalizing the processed electrical signal, providing a multiplier which is the reciprocal of the normalized processed electrical signal, and providing a gain corresponding to the multiplier.

* * * * *